United States Patent
Wharton et al.

(10) Patent No.: US 12,090,237 B2
(45) Date of Patent: Sep. 17, 2024

(54) BATTERY-ACTIVATED METAL IONIC ANTIMICROBIAL SURFACES

(71) Applicant: Aionx Antimicrobial Technologies, Inc., Hershey, PA (US)

(72) Inventors: Christopher M. Wharton, Hershey, PA (US); Zackary G. Lowe, Hershey, PA (US); Charles G. Rudolf, Hershey, PA (US); Thomas A. Fuller, Hershey, PA (US); David K. Tabbutt, Hershey, PA (US); Mark D. Loewen, Hershey, PA (US); Seth R. Zimmerman, Hershey, PA (US)

(*) Notice: Subject to any disclaimer, the term of this patent is extended or adjusted under 35 U.S.C. 154(b) by 0 days.

(21) Appl. No.: 17/606,357

(22) PCT Filed: Apr. 23, 2020

(86) PCT No.: PCT/US2020/029589
§ 371 (c)(1),
(2) Date: Oct. 25, 2021

(87) PCT Pub. No.: WO2020/219725
PCT Pub. Date: Oct. 29, 2020

(65) Prior Publication Data
US 2022/0143233 A1 May 12, 2022

Related U.S. Application Data

(60) Provisional application No. 62/837,618, filed on Apr. 23, 2019.

(51) Int. Cl.
*B01J 19/08* (2006.01)
*A61L 2/03* (2006.01)
*A61L 2/238* (2006.01)

(52) U.S. Cl.
CPC .......... *A61L 2/03* (2013.01); *A61L 2/238* (2013.01); *A61L 2202/14* (2013.01)

(58) Field of Classification Search
CPC .. A61L 2/03; A61L 2/238; H01J 27/22; H01J 27/26; H01J 27/022
(Continued)

(56) References Cited

U.S. PATENT DOCUMENTS

| 2,042,534 A | 6/1936 | Krause |
| 4,291,125 A | 9/1981 | Greatbatch |

(Continued)

FOREIGN PATENT DOCUMENTS

| WO | 2013144627 | 10/2013 |
| WO | WO 2017/218238 A1 | 12/2017 |
| WO | WO 2018/075259 A1 | 4/2018 |

OTHER PUBLICATIONS

PCT International Search Report for PCT/US2020/029589, filed Apr. 23, 2020, dated Jul. 1, 2020, 2 pages.
(Continued)

*Primary Examiner* — Monzer R Chorbaji
(74) *Attorney, Agent, or Firm* — Husch Blackwell LLP

(57) ABSTRACT

A metal ionic antimicrobial surface configured for external use on a surface location in an indoor environment. A surface structure includes a pair of opposed major surfaces, one surface forming an exposed layer having a pattern of conductive strips and corresponding insulative spacings with a power pod structure secured to the surface structure. The power pod structure houses a battery and a power control circuit electrically connected to the conductive strips. In embodiments, the battery has an amp-hour capacity of 150-1500 mAh, an average width of each conductive strip of copper and silver metallic ions and each insulative spacing is between 0.1 to 0.5 millimeters, and the power
(Continued)

control circuit includes a voltage booster circuit that maintains a constant low voltage of 2.5V-4.5V. The antimicrobial surface provides a replaceable period of at least a month of generally continuous and consistent reduction in microbial contaminants when positioned on surface locations that correlate to a zone of high impact regions for transmission pathways of microbial contaminants. In embodiments, a continuous reduction of at least 99% in microbial contaminants and at least a 2× reduction in other contaminated surfaces in a zone within the indoor environment proximate the antimicrobial surface is achieved over the replaceable period.

19 Claims, 15 Drawing Sheets

(58) Field of Classification Search
USPC .................... 422/32, 186.04, 186.05, 186.15
See application file for complete search history.

(56) References Cited

U.S. PATENT DOCUMENTS

| | | | |
|---|---|---|---|
| 5,324,275 | A | 6/1994 | Raad et al. |
| 5,328,451 | A | 6/1994 | Davis et al. |
| 5,759,564 | A | 6/1998 | Milder et al. |
| 6,500,165 | B1 | 12/2002 | Frank |
| 7,172,734 | B1 | 2/2007 | Joshi |
| 7,635,450 | B2 | 12/2009 | Goswami |
| 7,704,754 | B2 | 4/2010 | Malak |
| 7,931,858 | B1 | 4/2011 | Gross et al. |
| 8,106,367 | B2 | 1/2012 | Riskin |
| 8,118,791 | B2 | 2/2012 | Flick et al. |
| 8,135,466 | B2 | 3/2012 | Fuller et al. |
| 8,609,036 | B2 | 12/2013 | Fuller et al. |
| 8,620,431 | B2 | 12/2013 | Fuller et al. |
| 8,809,802 | B2 | 8/2014 | Sung et al. |
| 9,008,770 | B2 | 4/2015 | Fuller et al. |
| 9,289,520 | B2 | 3/2016 | Abraham et al. |
| 9,421,285 | B2 | 8/2016 | Fuller et al. |
| 9,561,294 | B2 | 2/2017 | Fuller et al. |
| 9,561,295 | B2 | 2/2017 | Fuller et al. |
| 9,566,359 | B2 | 2/2017 | Fuller et al. |
| 9,757,487 | B2 | 9/2017 | Roy et al. |
| 9,849,282 | B2 | 12/2017 | Fuller et al. |
| 9,950,086 | B2 | 4/2018 | Robert |
| 10,124,083 | B2 | 11/2018 | Robert |
| 2007/0141434 | A1 | 6/2007 | Joshi et al. |
| 2010/0163325 | A1 | 6/2010 | Reddy et al. |
| 2012/0164201 | A1 | 6/2012 | Harris |
| 2013/0064726 | A1 | 3/2013 | Morfill et al. |
| 2015/0125342 | A1 | 5/2015 | Abraham et al. |
| 2016/0138150 | A1 | 5/2016 | Pershin et al. |
| 2017/0136210 | A1 | 5/2017 | Robertson et al. |
| 2017/0165384 | A1* | 6/2017 | Fuller .................. E05B 1/0069 |
| 2017/0173218 | A1 | 6/2017 | Nazarian et al. |
| 2017/0224856 | A1 | 8/2017 | Mazzeo et al. |
| 2018/0008737 | A1 | 1/2018 | Roy et al. |
| 2019/0046006 | A1 | 2/2019 | Dorin |
| 2019/0194865 | A1 | 6/2019 | Russell et al. |
| 2020/0289697 | A1 | 9/2020 | Ando et al. |

OTHER PUBLICATIONS

PCT Written Opinion of the ISA for PCT/US2020/029589, filed Apr. 23, 2020, dated Jul. 1, 2020, 8 pages.

Reynolds, KA et al., "Microbial transmission in an outpatient clinic and impact of an intervention with an ethanol-based disinfectant," American Journal of Infection Control, vol. 47, No. 2, (Sep. 2018) pp. 128-132.

English, KM et al., "Contact among healthcare workers in the hospital setting: developing the evidence base for innovative approaches to infection control," BMC Infection Diseases, vol. 18, No. 1, (Apr. 2018) p. 184.

Rutala, WA et al., "Enhanced disinfection leads to a reduction of microbial contamination and a decrease in patient colonization and infection," Infection Control & Hospital Epidemiology, vol. 39, No. 184, (Jul. 2018) pp. 1118-1121.

Alexander, J., "History of the Medical Use of Silver", Surgical Infections, vol. 10, No. 3, pp. 289-292 (2009).

Grass, G., "Metallic Copper as an Antimicrobial Surface," Applied and Environmental Microbiology, vol. 77, No. 5, pp. 1541-1547 (2011).

Samberg, M.E., et al., "Biocompatibility analysis of an electrically-activated silver-based antibacterial surface system for medical device applications," Journal of Material Science: Material Medicine, vol. 24, No. 3 (Dec. 2012) pp. 755-760.

Shirwaiker RA et al., Abstract of "Micro-scale fabrication and characterization of a silver-polymer based electrically activated antibacterial surface," Biofabrication, vol. 3, No. 1 (2012), p. 015003.

Shirwaiker RA, "The characterization of the antibacterial efficacy of an electrically activated silver ion-based surface system," University Park: The Pennsylvania State University, 2011.

Esolen, LM et al., "The efficacy of self-disinfecting bedrail covers in an intensive care unit," American Journal of Infection Control, vol. 1, No. 5 (Nov. 2017) pp. 417-419.

Agile Sciences "Test Protocol for Verifying Antimicrobial Effectiveness on Printed Surfaces", Oct. 2014, 12 pgs. Bacteria, available at https://aionx.com/wp-content/uploads/2019/05/2a-Bacteria-lab.pdf. Accessed Jul. 20, 2023.

Utah State University, "Virucidal Efficacy Assay", Jun. 6, 2019, 7 pgs. Viral available at https://aionx.com/wp-content/uploads/2020/02/AIONX_Antimicrobial_Technologies_Study_by_Institute_for_Antiviral_Research.pdf . Accessed Jul. 20, 2023.

Utah State University, "Virucidal Efficacy Assay", Apr. 2, 2020. Viral available at https://aionx.com/wp-content/uploads/2020/04/REPORT_AIONX-2020.pdf. Accessed Jul. 20, 2023.

Aionx Antimicrobial Technologies, Inc., "Test Protocol for Verifiying Antimicrobial Effectiveness of RPET, 82uA Circuits, Clostridium difficile-spore form", Dec. 2017-Jan. 2018, 9 pgs. C. diff spores. available at https://aionx.com/wp-content/uploads/2019/05/2c-C-diff-lab.pdf. Accessed Jul. 20, 2023.

Samberg, et al., "Biocompatability analysis of an electrically-activated silver-based antibacterial surface system for medical device applications". J. Mater Sci: Mater Med, Dec. 16, 2012, 7 pgs. Biocompatibility study. available at http://www.dtic.mil/get-tr-doc/pdf?AD=ADA615774. Accessed Jul. 21, 2023.

Rutala, et al., "Enhanced disinfection leads to reduction of microbial contamination and a decrease in patient colonization and infection", Infection Control & Hospitality Epidemiology (2018), 39, 1118-1121. Reduced Environmental Contamination Correlates with Reduced Infection Rate. available at http://tru-d.com/wp-content/uploads/2018/10/BETRD-III_Rutala_2018.pdf. Accessed Jul. 21, 2023.

* cited by examiner

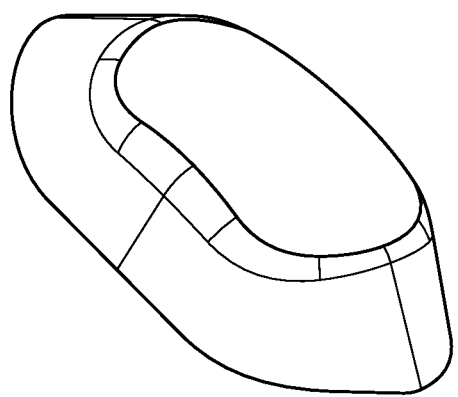
FIG. 4A
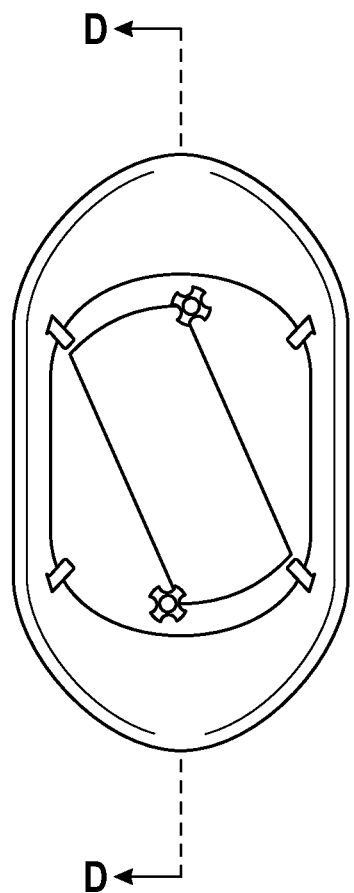
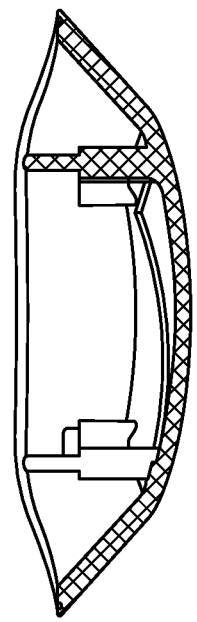
FIG. 4B
FIG. 4C

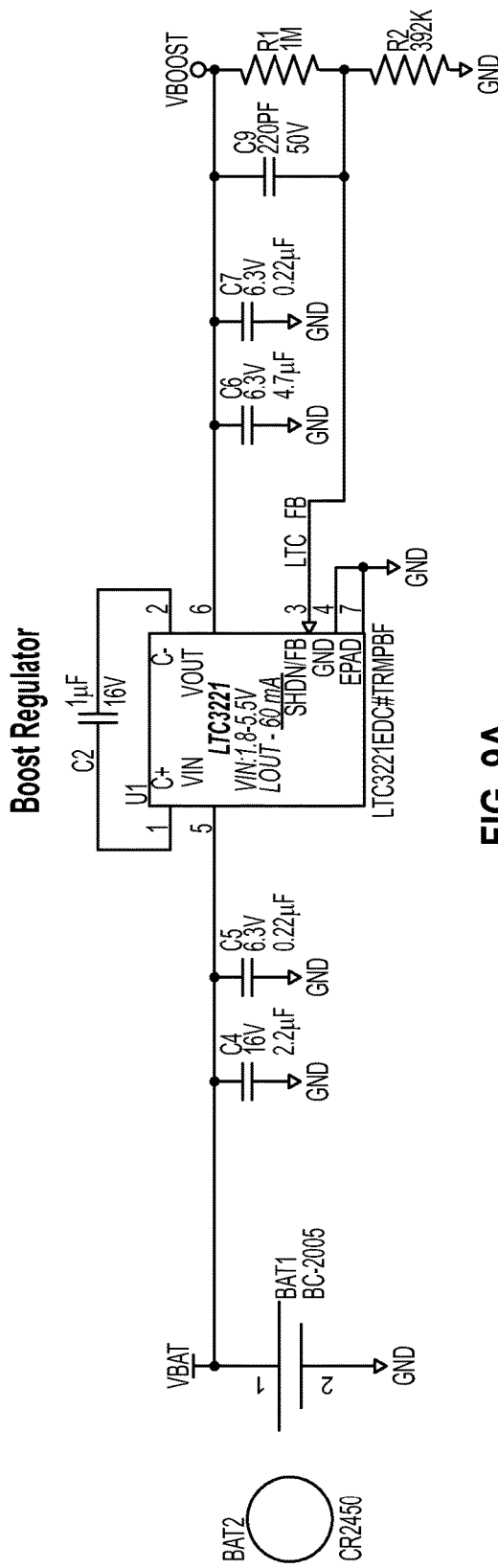
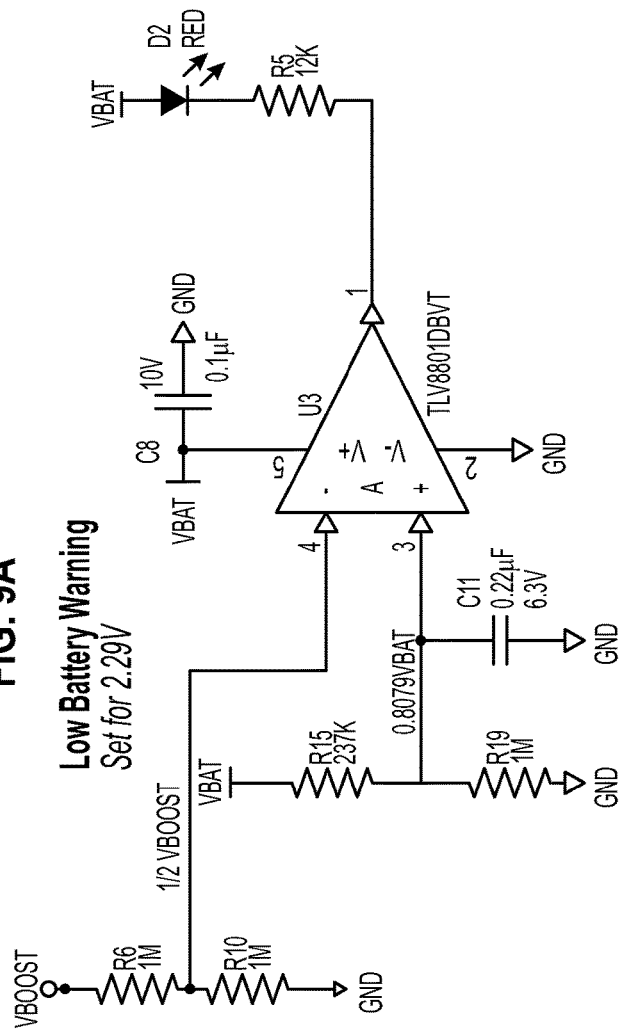
FIG. 9A
FIG. 9B

BATTERY-ACTIVATED METAL IONIC ANTIMICROBIAL SURFACES

RELATED APPLICATIONS

This present disclosure claims priority to U.S. Provisional Application No. 62/837,618 filed Apr. 23, 2019, and PCT International Application No. PCT/US2020/029589, filed Apr. 23, 2020, both of which are entitled "IMPROVED BATTERY-ACTIVATED METAL IONIC ANTIMICROBIAL SURFACES", the entire disclosures of which hereby incorporated by reference.

FIELD OF THE INVENTION

The present disclosure relates generally to methods and apparatus for sterilizing and disinfecting materials utilizing electric current and oligodynamic metallic ions. More particularly, the present disclosure relates to battery-activated metal ionic antimicrobial surfaces for external use in an indoor environment in which microbial contamination may be found.

BACKGROUND OF THE INVENTION

Numerous studies and reports have demonstrated the significance of healthcare environments in the transmission of microbial contamination. Reynolds, K A et al., "Microbial transmission in an outpatient clinic and impact of an intervention with an ethanol-based disinfectant," *American Journal of Infection Control*, Vol. 47, No. 2, (September 2018) pp. 128-132; English, K M et al., "Contact among healthcare workers in the hospital setting: developing the evidence base for innovative approaches to infection control," *BMC Infection Diseases*, Vol. 18, No. 1, (April 2018) pp. 184; Rutala, W A et al., "Enhanced disinfection leads to a reduction of microbial contamination and a decrease in patient colonization and infection," *Infection Control & Hospital Epidemiology*, Vol. 39, No. 184, (July 2018) pp. 1118-1121. Conventionally, infection control in an in vivo or internal context is managed by the use of antibiotics and microbial growth in an ex vivo or external context is managed by manual cleaning with repeated episodic uses of disinfectant chemicals and cleaners.

The use of the oligodynamic effect of metallic ions to inhibit microbial growth, including bacterial, fungal, algae, mold and mildew, has long been known. In contrast to antibiotics or chemical agents which often possess a single mode of action making the development of bacterial resistance easier, development of resistance to metallic ions is more difficult because metal ions attack and kill microbes in different simultaneous ways. The metallic ions can cause a breakdown of cell-supporting function by inhibition of transmembrane transport and by inactivating intracellular enzymes. In addition, some metallic ions can interfere with cell reproduction. The metals used as the antibacterial metal are noble metals, typically silver or copper. See, Alexander, J., "History of the Medical Use of Silver", *Surgical Infections*, Vol, 10, No. 3, pp. 289-292 (2009); Grass, G., "Metallic Copper as an Antimicrobial Surface," *Applied and Environmental Microbiology*, Vol. 77, No. 5, pp. 1541-1547 (2011).

A passive oligodynamic effect typically involves coatings or solutions of noble metals that rely on the chemical induction of local galvanic current or a natural oxidative process to electrochemically release the metallic ions. In contrast, an active oligodynamic effect also utilizes electrical activation to enhance the release of the metallic ions and also to provide a directed flow of those metallic ions.

Some older prior art systems and techniques describe the use of an active oligodynamic effect in the context of antimicrobial treatments of liquids, plants or animals, such as are shown in U.S. Pat. Nos. 2,042,534 and 4,291,125. More recent prior art systems and techniques describe the use of an active oligodynamic effect for antimicrobial purposes in a medical context in the form of implants or in vivo procedures. Examples for use with catheters are shown in U.S. Pat. Nos. 5,324,275, 5,328,451 and U.S. Publ. Appl. No. 2017/0136210 A1. Other examples for use with orthopedic implants are shown in U.S. Pat. Nos. 6,500,165, 8,620,431, 9,008,770, 9,421,285, and 9,849,282.

Although there are some common aspects between implanted or in vivo types of electrically activated oligodynamic systems and external or ex vivo types of activate oligodynamic systems for antimicrobial purposes, there are significant differences. For example, the difference in a generally wet environment for internal usage for versus a generally dry environment for external usage, as well as the different nature and duration of the amount of tissue contact with the surfaces of such systems impose different demands on the design of the electrical activation of such systems. In addition, the complex and often unpredictable characteristics of the amount and types of the multitudes of microbial organisms that may be encountered by a battery-activated metal ionic antimicrobial surface for external use in an indoor environment in which microbial contamination may be found must be addressed.

Earlier experiments with electrically-activated silver-based antibacterial systems to address these kinds of external infections and contamination were reported in Samberg, M. E., et al., "Biocompatibility analysis of an electrically-activated silver-based antibacterial surface system for medical device applications," *Journal of Material Science: Material Medicine*, Vol. 24, No. 3 (December 2012) pp. 755-60; Shirwaiker R A et al., "Micro-scale fabrication and characterization of a silver-polymer based electrically activated antibacterial surface," *Biofabrication*, Vol. 3, No. 1 (2012), pp. 015003; and Shirwaiker R A, "The characterization of the antibacterial efficacy of an electrically activated silver ion-based surface system," *University Park: The Pennsylvania State University*, 2011.

A metal ionic antimicrobial surface for external use in a health-related environment has been developed by the assignee of the present disclosure in the form of periodically replaceable battery-activated metal ionic antimicrobial surfaces that are marketed under the trademark Clean Surfaces™ (http://aionx.com/technology/), various aspects of which are described in U.S. Pat. Nos. 8,609,036, 9,561,294, 9,561,295, and 9,566,359. Results of an experiment based on an early version of this technology were reported in Esolen, L M et al., "The efficacy of self-disinfecting bedrail covers in an intensive care unit," *American Journal of Infection Control*, Vol. 1, No. 5 (November 2017) pp. 417-19. There are opportunities, however, to improve on the design and implementation of this kind of periodically replaceable battery-activated metal ionic antimicrobial surface for external use in an indoor environment.

SUMMARY OF THE INVENTION

A periodically replaceable battery-activated metal ionic antimicrobial surface for external use in an indoor environment in which microbial contamination may be found in accordance with embodiments as disclosed provides for more consistent effectiveness and longevity over an operational period of at least a month. In various embodiments, the antimicrobial surface is formed of a pattern of conductive strips separated by corresponding insulative spacings between adjacent strips on one or more surfaces. In embodiments, the surfaces are configured for external use in an indoor environment and include a base material layer, an insulating layer, and an exposed layer on which the pattern of conductive strips and insulative spacings are disposed. The electrical activation that generates an active oligodynamic effect of the antimicrobial surface in various embodiments is provided by a power pod that houses a battery and a power control circuit that is electrically connected to the conductive strips on the surface.

In embodiments, the power pod is physically secured to the antimicrobial surface on a portion of an exposed layer to allow the base material layer of the surface to conform to a corresponding surface of an article in the environment is covering, such as a flat working surface, a bed rail, an overbed table, a sink surround, a door push plate, a floor mat, a locker surface, or the like. In some embodiments, the power pod is self-contained and not intended for user access or replacement of the battery housed in the pod. In some embodiments, the power pod is designed to be recycled to recover and reuse the power control circuit.

For implanted or in vivo medical procedures, the practical design limits for the current and/or voltage of electrical activation needed for an active oligodynamic effected are different than for external or ex vivo related usages. Examples of external or ex-vivo usages in an indoor environment in which microbial contamination may be found can include medical, health, wellness, sanitation, food preparation, or fitness contexts. Examples of such indoor environments can include a hospital, clinic, emergency room, nursing home, doctor's office, gym, locker room, training or rehabilitation facility, bathroom, kitchen, dining room or the like.

In various embodiments, such indoor environments can be considered health-related as an objective is to reduce microbial contamination within the indoor environment so as to improve the quality of life and wellness of the humans using the indoor environment.

In various embodiments, the indoor environment can be within a room or an area of a facility or building. In various embodiments, the indoor environment includes one or more high impact regions or portions of a room or area of the indoor environment that may be transmission pathways of microbial contaminants. To be efficacious over a predetermined minimum longevity for these types of usages and environments, a battery-activated metal ionic antimicrobial surface must be designed to safely handle various intermittent contacts with multiple humans and/or contaminants on a variety of different kinds of surfaces and/or apparatus that can occur in such an indoor environment.

In vivo medical procedures or implants deal with a single patient and a relatively known set of environmental conditions. Typically, once an in vivo infection is treated and the microbes killed, there is limited opportunity for reinfection. In a typical indoor environment, however, there are repeated and effectively continuous opportunities for infection and contamination. There also is no single set of conditions for which an active oligodynamic effect will need to be designed as the indoor environment can include multitudes of different people and different features, furnishings, equipment and even different environmental aspects of the indoor environment. Each person will have different electrical characteristics and sensitivities to the perception of an electrical shock, for example. In addition, factors in the environmental conditions, such as temperature and humidity, and even differences in the types of floor or materials of other surfaces in the indoor environment can impact the range of different electrical environments in which a battery-activated metal ionic antimicrobial surface must operate. Another consideration is the need for more consistent operational longevity that can provide effective antimicrobial effects by a periodically replaceable battery-activated metal ionic antimicrobial surface for a predetermined minimum period of usage in an indoor environment of at least a month.

Various embodiments are disclosed for the design and configuration of the components of a power pod that meet the efficiency, safety and longevity requirements over the range of electrical, environmental and contaminant environments that may be encountered by a periodically replaceable battery-activated metal ionic antimicrobial surface for external use in a health-related environment. In embodiments, the power pod structure houses a battery and a power control circuit that is electrically connected to battery and to the conductive strips on the exposed layer. In embodiments, the battery has an amp-hour electrical storage capacity of between 150 to 1500 mAh. In embodiments, the battery is a 3V lithium coin type battery and, more particularly, having an amp-hour electrical storage capacity between 500-750 mAH. In embodiments, the power control circuit includes a voltage booster circuit that maintains a constant but relatively lower voltage of between about 2.5V to 4.5V to achieve a longer period of continuous and consistent operational effectiveness above battery voltages of about 1.8V to 2.0V. In embodiments, the power control circuit optional includes one or more of a current limiting circuit, a low battery indicator circuit and a polarity inversion circuit. In embodiments, the polarity inversion circuit may implement an inversion cycle every 100-200 seconds, and more particularly between 150-180 seconds. In embodiments, the power control circuit includes a chopper circuit. In some embodiments, the power control circuit may include a microcontroller or state machine controller provided power, longevity and cost requirements can still be achieved with the incorporation of such a circuit control element.

In various embodiments, the effectiveness of the periodically replaceable battery-activated metal ionic antimicrobial surface battery-activated metal ionic antimicrobial surface provides a significant and continuous reduction in microbial contamination in indoor environments over the replaceable period of at least a month when the antimicrobial surface is located in positions that correlate to high impact regions for the contamination transmission pathways in that environment. In various tests and experiments, the use of various embodiments resulted in a reduction of at least a 99% continuous reduction in microbial contaminants on the surface structure after exposure to such microbial contaminants and at least a 2× reduction in a number of other contaminated surfaces within a zone within an indoor environment. In some embodiments, the zone is coextensive with a given room. In other embodiments, the zone has a radius of at least 1 m and up to 5 m from the device.

In various tests and experiments, the use of various embodiments resulted in at least a 99% reduction in bacterial contaminants on the antimicrobial surface within less than an hour after exposure to such bacterial contaminants. In embodiments, a test protocol demonstrated a 6 log 10 reduction of E. coli in 5 minutes and up to 5 log 10 reduction of MRSA in 10 minutes. In various tests and experiments, the use of various embodiments resulted in at least a 99% reduction within less than a day in viral contaminants on the antimicrobial surface. In embodiments, a test protocol demonstrated a 2 log 10 reduction of murine norovirus. In various tests and experiments, the use of various embodiments resulted more than 95% reduction in spore-based contaminants on the antimicrobial surface. In embodiments, a test protocol demonstrated up to 1.46 log 10 reduction of C. diff. spores.

BRIEF DESCRIPTION OF THE DRAWINGS

FIG. 4A-4C illustrate an isometric view, a top view and a cross-sectional view of an embodiment of a power pod for a battery-activated metal ionic antimicrobial surface in accordance with one embodiment.

FIGS. 9A and 9B are electrical schematic diagrams of a boost regulator and a low battery indication of the power control circuit in accordance an embodiment.

Figure 1A:
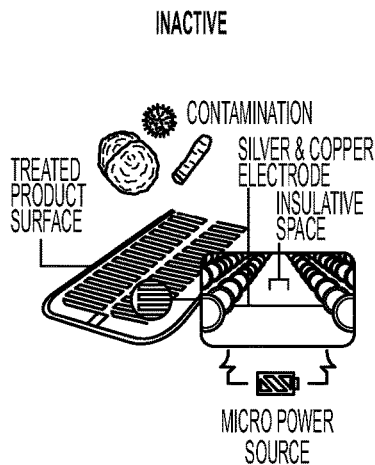
FIG. 1A-1C are schematic illustrations of the operation of a prior art battery-activated metal ionic antimicrobial surface.

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION OF THE EMBODIMENTS

Disclosed herein is an improved device that provides a battery-activated metal ionic antimicrobial surface for external use in an indoor environment, such as a health-related environment Embodiments disclosed herein provide for increased effectiveness with more predictable operational longevity. In various embodiments, the device includes a surface structure defining a pair of opposed major surfaces separated by a thickness and a power pod structure physically secured to the surface structure.

In embodiments, the surface structure can include a first of the pair opposed major surfaces that forms a base material layer configured to be positioned on at least a portion of the surface of the apparatus in the indoor environment, a second of the pair opposed major surfaces that forms an exposed layer having a pattern of conductive strips separated by corresponding insulative spacings between adjacent conductive strips, and an insulating layer disposed between the base material layer and the exposed layer. In embodiments, the conductive strips and the insulative spacings between adjacent conductive strips have average widths of between 0.1 to 0.5 millimeters (0.005 to 0.04 inches). In one embodiment, the conductive strips have average widths of 0.25 millimeters and the insulative spacings between adjacent conductive strips have average widths of 0.375 millimeters. In embodiments, the conductive strips are screen printed using a conductive ink and have a thickness when printed of between 0.01-0.05 millimeters. In one embodiment, the conductive strips have an average thickness of about 0.025 millimeters.

In embodiments, the power pod structure is physically secured to the surface structure on a portion of the exposed layer. In embodiments, the power pod structure houses a battery and a power control circuit that is electrically connected to battery and to the conductive strips on the exposed layer. In embodiments, the power pod structure has a volume that ranges from 100-250 cubic centimeters. In embodiments, the power pod structure has a mating structure that is sufficiently flexible to be pressure mounted to the surface structure.

In embodiments, the battery has an amp-hour electrical storage capacity of between 150 to 1500 mAh. In some embodiments, the battery is a 3V lithium coin type battery and, more particularly, having an amp-hour electrical storage capacity between 500-750 mAH. In other embodiments, the battery may be a combination of one or more battery cells that provides the electrical storage capacity and continuous current draw capability in an arrangement of one or more cells have a total physical volume of 25-125 cubic centimeters.

In embodiments, the power control circuit includes a voltage booster circuit that maintains a constant but relatively lower voltage of between about 2.5V to 4.5V to achieve a longer period of continuous and consistent operational effectiveness. In one embodiment, the voltage booster circuit maintains a voltage of 3.7V until the battery supply voltage drops below 1.8V. In another embodiment, the voltage booster circuit maintains a voltage of 4.3V until the battery voltage drops below 2.0V. In embodiments, the voltage booster circuit maintains a desired voltage within +/−0.25V. In some embodiments, the voltage booster circuit maintains a desired voltage within +/−0.1V.

In embodiments, the power control circuit optional may include one or more of a current limiting circuit, a low battery indicator circuit and a polarity inversion circuit. In embodiments, the polarity inversion circuit may implement an inversion cycle every 100-200 seconds, and more particularly between 150-180 seconds as described in more detail hereinafter. In embodiments, the power control circuit includes a chopper circuit. In some embodiments, the power control circuit includes a microcontroller or state machine controller provided power, longevity and cost requirements can still be achieved with the incorporation of such a circuit control element.

In embodiments, the conductive strips are formed of a polymer material doped with metallic particles or flakes that can be screen printed on the exposed layer of the surface structure, with the metallic ions released by the particles or flakes being a mixture of silver and copper. In embodiments, the doping of metallic ions in the polymer material is a metallic doped polymer in which silver is 20-30% of a 90-95% cured metallic polymer, which translates to 10%-30% silver at the exposed surface, with about 65%-75% copper in the cured ink.

Figure 1B:
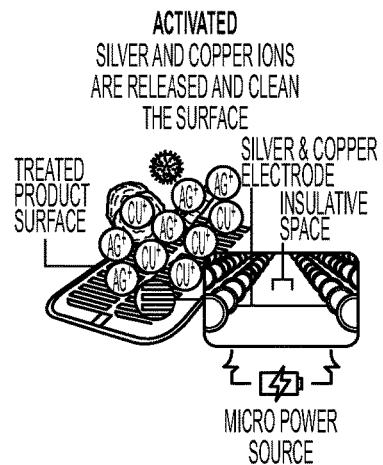
Figure 1C:
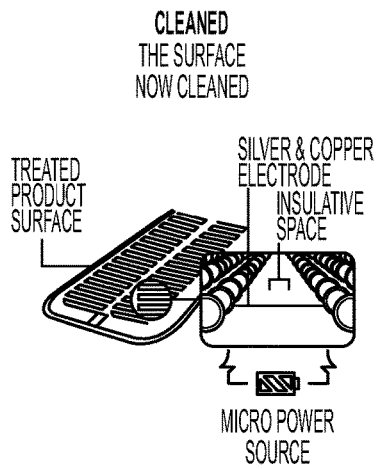

The process by which a battery-activated metal ionic antimicrobial surface achieves an active oligodynamic effect for antimicrobial purposes is shown in FIGS. 1A-1C. A pattern of strips of copper and silver electrodes are disposed on a surface that can be exposed to contaminants such as microbes or pathogens as shown in FIG. 1A. The electrodes in the strips are electrically connected to a micro power source, such as a battery. Once the battery is activated as shown in FIG. 1B, metallic ions are released into the areas in which the contaminants are present to form a completed electrical circuit, thereby providing an antimicrobial effect on the contaminants. Once the contaminants are substantially killed or destroyed, the electrical circuit that had been completed by the contaminants is opened and the battery is disconnected as shown in FIG. 1C.

Figure 2A:
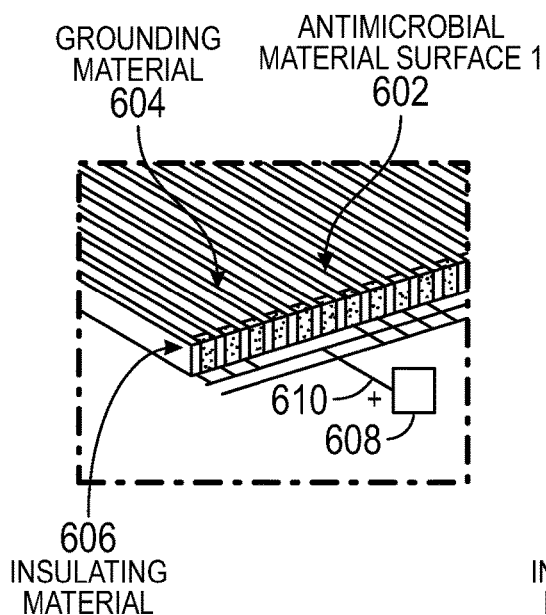
FIG. 2A-2B illustrate cross-sectional side views of embodiments of the prior art battery-activated metal ionic antimicrobial surface of FIG. 1A-1C.

The device disclosed herein improves upon the kind of battery-activated metal ionic antimicrobial surface that is disclosed in U.S. Pat. No. 8,609,036, which is hereby incorporated by reference herein. FIG. 2A illustrates an embodiment of a prior art metal ionic anti-microbial device in accordance with U.S. Pat. No. 8,609,036. The device 600 includes a plurality of antimicrobial metal components disposed on the external surface of a plurality of first elements 602, and a plurality of second elements 604, labeled "grounding material." Optionally, a plurality of second antimicrobial metal components is disposed on the external surface of at least one of the plurality of second elements. Each of the individual first and second elements are separated by an insulator 606. The size of the insulator and thus the size of the separation between an individual first element and an individual second element is selected to optimize an antimicrobial effect in general, an insulator is dimensioned such that an individual first element and an individual second element are separated by about 0.1 micron-10 cm. inclusive, although not limited to this range of sizes.

A power source 608 is connected to the device 600 such that one terminal of the power source is in electrical communication with the plurality of first elements and the plurality of first antimicrobial metal components. The second terminal of the power source is in electrical communication with the plurality of second elements.

In a further embodiment, an antimicrobial device is provided which includes a device body having a first element having a first external surface and a second element having a second external surface, a first metal component containing an antimicrobial metal disposed on the first external surface of the device body, a power source having a first terminal and a second terminal, the first terminal in electrical communication with the first metal component; and an insulator placed in a current path between the first terminal of the power source and the second terminal of the power source preventing current flowing from the first terminal from reaching the second terminal, wherein activation of the power source creates a potential between the first element and the second element such that placement of an object in contact with the antimicrobial metal results in movement of metal ions from the antimicrobial metal toward the object.

Figure 2B:
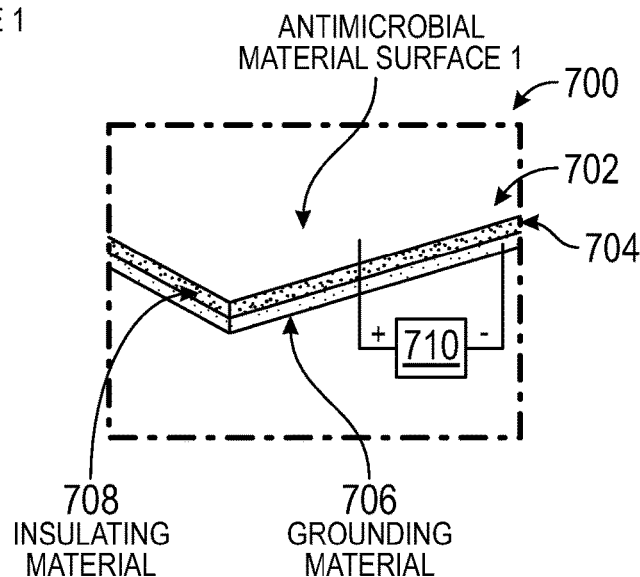

FIG. 2B illustrates another exemplary embodiment of the prior art metal ionic anti-microbial device in accordance with U.S. Pat. No. 8,609,036. An antimicrobial device 700 includes an antimicrobial metal component disposed on the external surface 702 of a first element 704. As described above, a first element and/or second element is optionally fabricated partially or wholly from an antimicrobial metal. A second element, 706, labeled "grounding material," is depicted and the first and second elements, 704 and 706, respectively, are separated by an insulator 708, labeled "insulating material" in FIG. 2B. The size of the insulator and thus the size of the separation between the first element and the second element is selected to optimize an antimicrobial effect. In general, an insulator is dimensioned such that an individual first element and an individual second element are separated by about 0.1 micron-10 cm, inclusive, although not limited to this range of sizes.

A power source 710 is connected to the device 700 such that one terminal of the power source is in electrical communication with the first element and the first antimicrobial metal component. The second terminal of the power source is in electrical communication with the second element. The device may be optionally directly grounded or may use a "floating" ground.

In the embodiment of the prior art metal ionic antimicrobial device such as shown in FIG. 2B, a potential is created between the antimicrobial metal 702 and the second element 706. When an object, not shown, which is neutral or negatively charged with respect to the surface 702 is placed in contact with the surface 702, metal ions from the antimicrobial metal move towards the object, providing an antimicrobial effect. It is noted that a circuit is not completed by the object in an embodiment as illustrated in FIG. 2B. The object is illustratively an object typically used in conjunction with the device or which otherwise comes in contact with the device.

Various embodiments of a battery-activated metal ionic antimicrobial surface device are disclosed as shown in FIG. 3A-3D that improve upon the prior art metal ionic antimicrobial device as shown in FIGS. 2A and 2B. In embodiments, the surface device is a disposable or replaceable device that may be used in a variety of healthcare settings for external use. The surface device provides generally continuous and consistent decontamination of the antimicrobial surfaces self-cleaning that maintains an efficacy over a period of use of at least a month. The surface device may be securely attached to and cover targeted high touch surfaces of medical apparatus. The surface device provides for generally continuous and consistent protection against contamination caused by environmental contamination and intermittent contact with health-related personal or patients between episodic cleaning or disinfection, even during active care hours.

In embodiments, the exterior portions of surface device are constructed of polymer or other similar materials arranged in a configuration that is generally resistant to common cleaners and disinfectants. In these embodiments, the use of surface device at a use site is intended to be a supplement to, and not a substitute for, standard infection control practices, and users, such as medical users, should continue to follow all current infection control practices, including those practices related to episodic cleaning and disinfection of environmental surfaces.

Figure 3A:
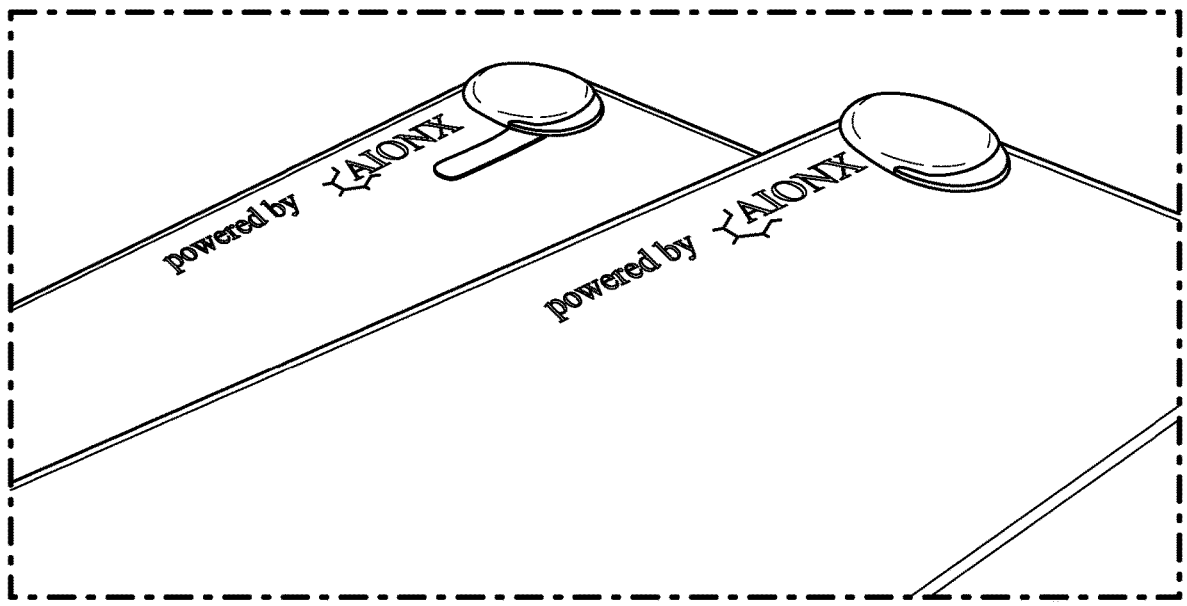
FIG. 3A-3D illustrate isometric views of a battery-activated metal ionic antimicrobial surface in accordance with various different embodiment.

FIG. 3A shows an embodiment of a generally flat and rectangular surface pad that may be placed and/or secured at work areas, such as stations, desks, counters or other flat areas, where healthcare workers do charting or otherwise place work or personal items. Studies indicate that such work areas are a significant component of contamination transmission networks in a typical medical environment. In addition to self-cleaning of the surface pad, the electrically activated oligodynamic system provided by the surface pad also begins to clean the surfaces of items placed on the surface, such as smartphones, tablets, and stethoscopes. In various embodiments, the effective antimicrobial surface area of a surface pad can range from 500 sq. cm to 10,000 sq. cm. in size.

Figure 3B:
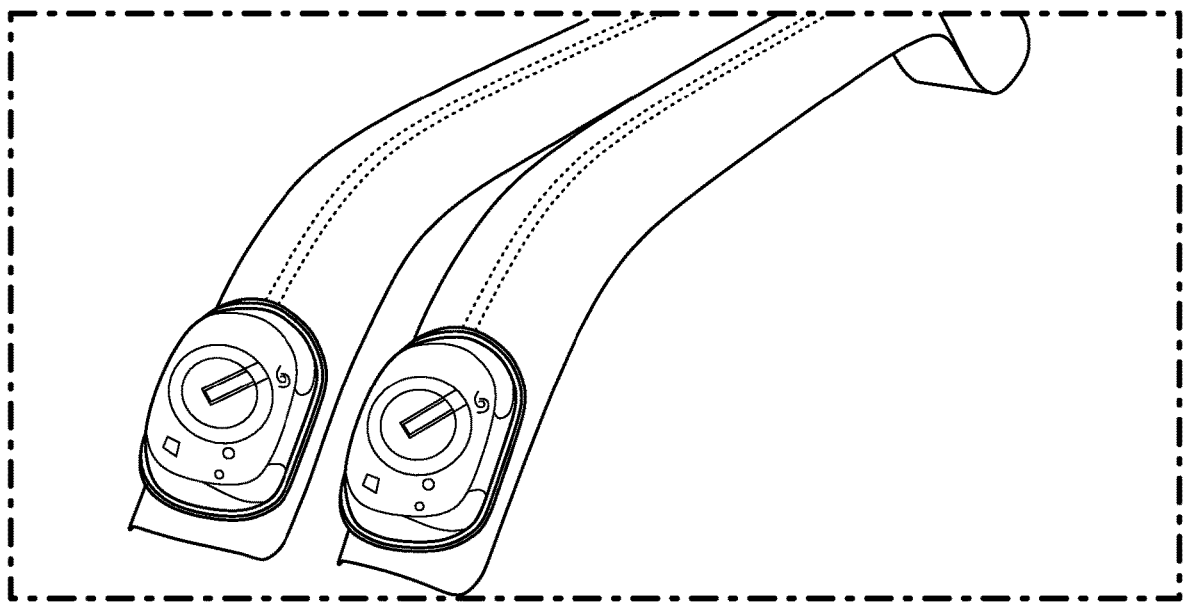

FIG. 3B shows an embodiment of a curved surface configured for attachment to a bedrail. Bedrails are more frequently touched by healthcare workers and more contaminated than any other surface in an indoor patient environment, such as a hospital room. In embodiments, the curved surface can be pre-formed to mechanically fit a given bedrail configuration to protect high touch areas of the bedrails. In other embodiments, the curved surface can be malleable and be wrapped at least partially around a given bedrail configuration. In other embodiments, a base layer of the curved surface may include portions that provide a tacky or adhesive quality to allow a user to adhere the curved surface to a given bedrail configuration. In one embodiment, an adhesive/tacky layer for a curved surface composed of a thermoformable adhesive, such as available from 3M 9172 MP-200 MP US.

Figure 3C:
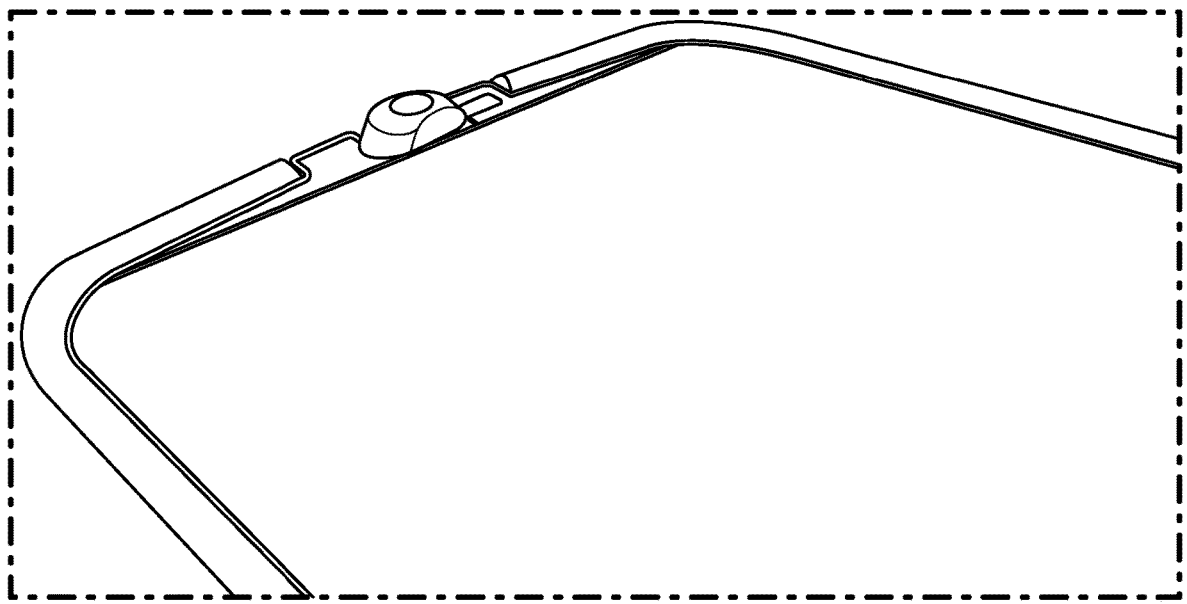

FIG. 3C shows an embodiment of a flat surface configured for placement or attachment to an overbed table or tray. Overbed tables are one of the most touched, most contaminated surfaces in the patient environment, whether they are used to hold patients' personal effects or as a staging area for healthcare workers. In embodiments, the flat surface can be pre-formed to mechanically fit within a perimeter or edge boundary of an upper surface of the overbed table. In other embodiments, the flat surface may have edges that are pre-formed to mechanically fit or wrap around the edges of the overbed table. In other embodiments, a base layer of the flat surface may include portions that provide a tacky or adhesive quality to allow a user to adhere the curved surface to a given portion of an overbed table. In one embodiment, an adhesive/tacky layer for a flat surface utilizing KiwoPrint D177-Rev_0 that is specifically 'thinned' for this embodiment and is rolled on rather than printed or sprayed on to the base layer.

Figure 3D:
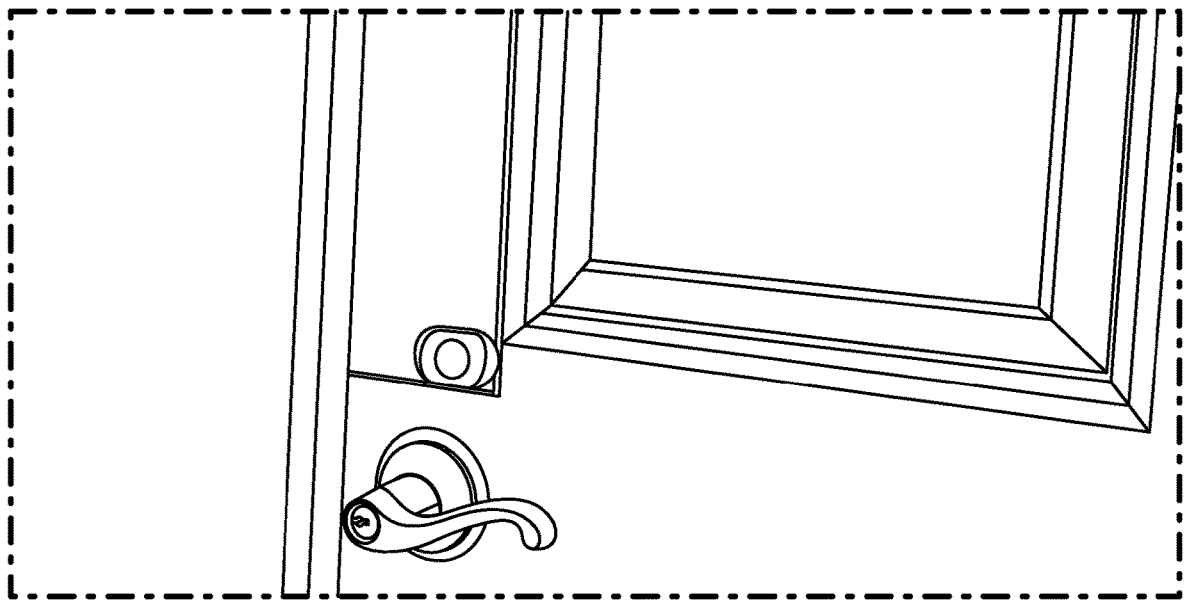
Figure 5A:
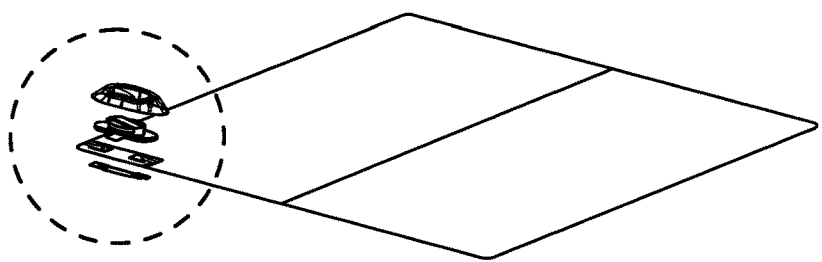
FIG. 5A-5B are isometric and exploded views of the attachment of the power pod of FIG. 4A-4C with the surface device of the embodiment of FIG. 3A.
Figure 5B:
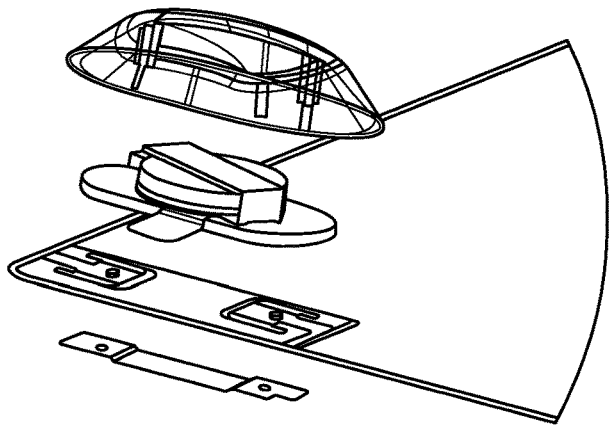
Figure 6A:
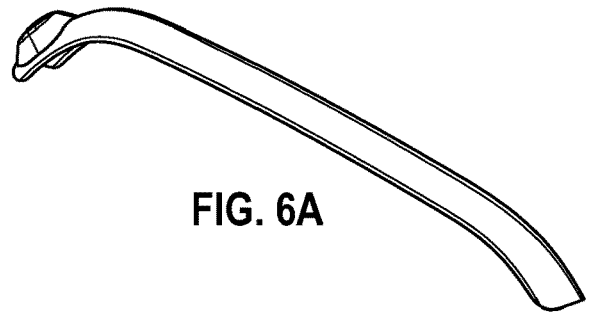
FIG. 6A-6C are isometric and exploded views of the attachment of the power pod of FIG. 4A-4C with the surface device of the embodiment of FIG. 3B.
Figure 6B:
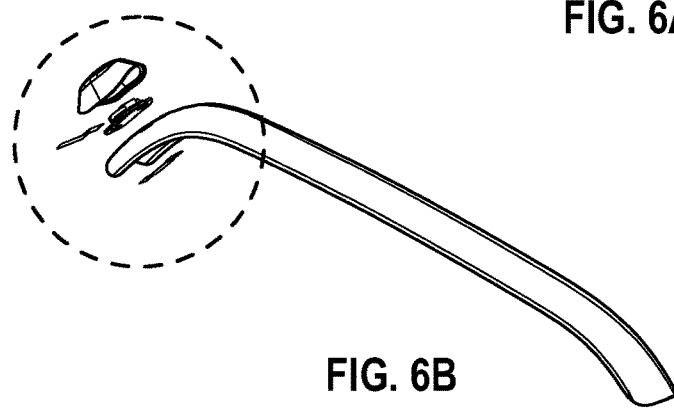
Figure 6C:
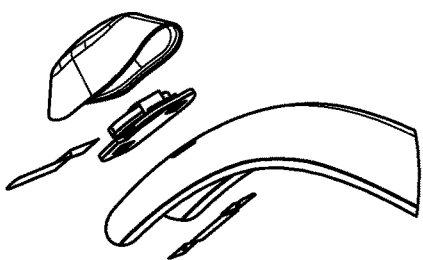

FIG. 3D shows an embodiment of a flat surface configured for placement or attachment to operate as a door push plate. Many hospital units have swinging doors to facilitate movement of healthcare workers. The push plates of these doors are typically touched every time a person enters or exits the room, making them a central node in the units' contamination transmission network. In embodiments, the door push plate can include clasps or attachment mechanism to be mechanically secured on a portion of the door. In other embodiments, a door push plate cover may include edges that are pre-formed to mechanically fit or wrap around the edges of an existing door push plate. In other embodiments, a base layer of the door push plate may include portions that provide a tacky or adhesive quality to allow a user to adhere the push plate surface to a given portion of a door or existing door push plate.

In embodiments, only a portion of the exposed surface of the surface substrate may be provided with the alternating pattern of conductive strips and insulative spacings that will be energized by the power control circuit as an effective active exposed surface area. In embodiments, the exposed surface area includes a total surface area of between 75 sq.cm to 10,000 sq.cm to permit easy replaceability of the substrate surface on a periodic basis. The maximum effective active exposed surface area corresponds to an area over which the surface current generated by the power pod can ensure a desired kill over the entire area for the operational period of the replaceable surface structure.

Referring to FIG. 4A-4C, an embodiment of the power pod structure is depicted. In embodiments, the power pod structure of FIG. 4A mates with a corresponding perimeter structure defined on the exposed layer of the surface structure as shown in FIGS. 5A-5B and FIGS. 6A-6C. In embodiments, the perimeter structure is defined as an edge onto which a resilient edge of the power pod structure is forced down onto by the engagement and securing of the retention posts as described below. In other embodiments, the perimeter structure may include a peripheral edge feature to align and optionally further secure the power pod structure to the surface structure.

Figure 7A:
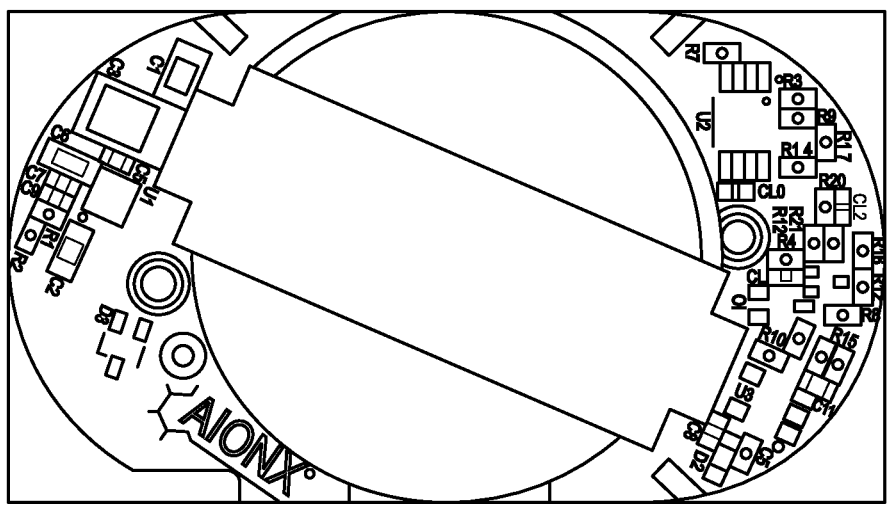
FIGS. 7A and 7B are top and bottom plan view of an embodiment of a printed circuit board and battery of the power pod of FIG. 4A-4C.
Figure 7B:
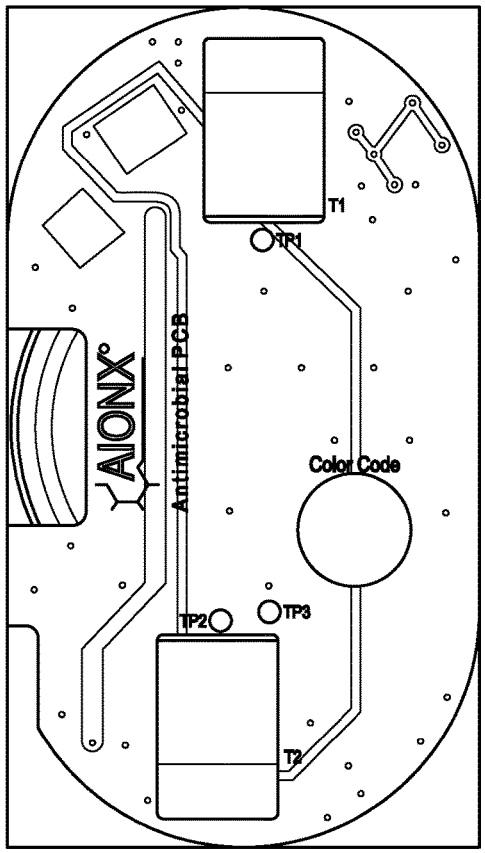
Figure 8A:
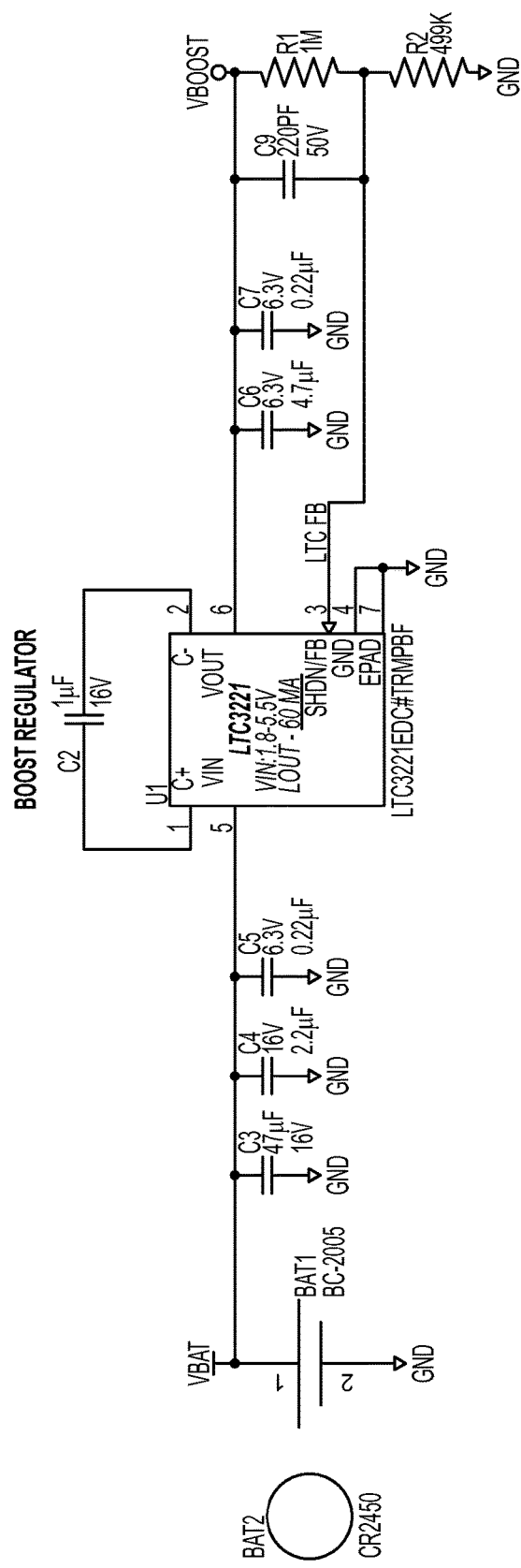
FIGS. 8A and 8B are electrical schematic diagrams of a boost regulator and a low battery indicator of the power control circuit in accordance with an embodiment.
Figure 8B:
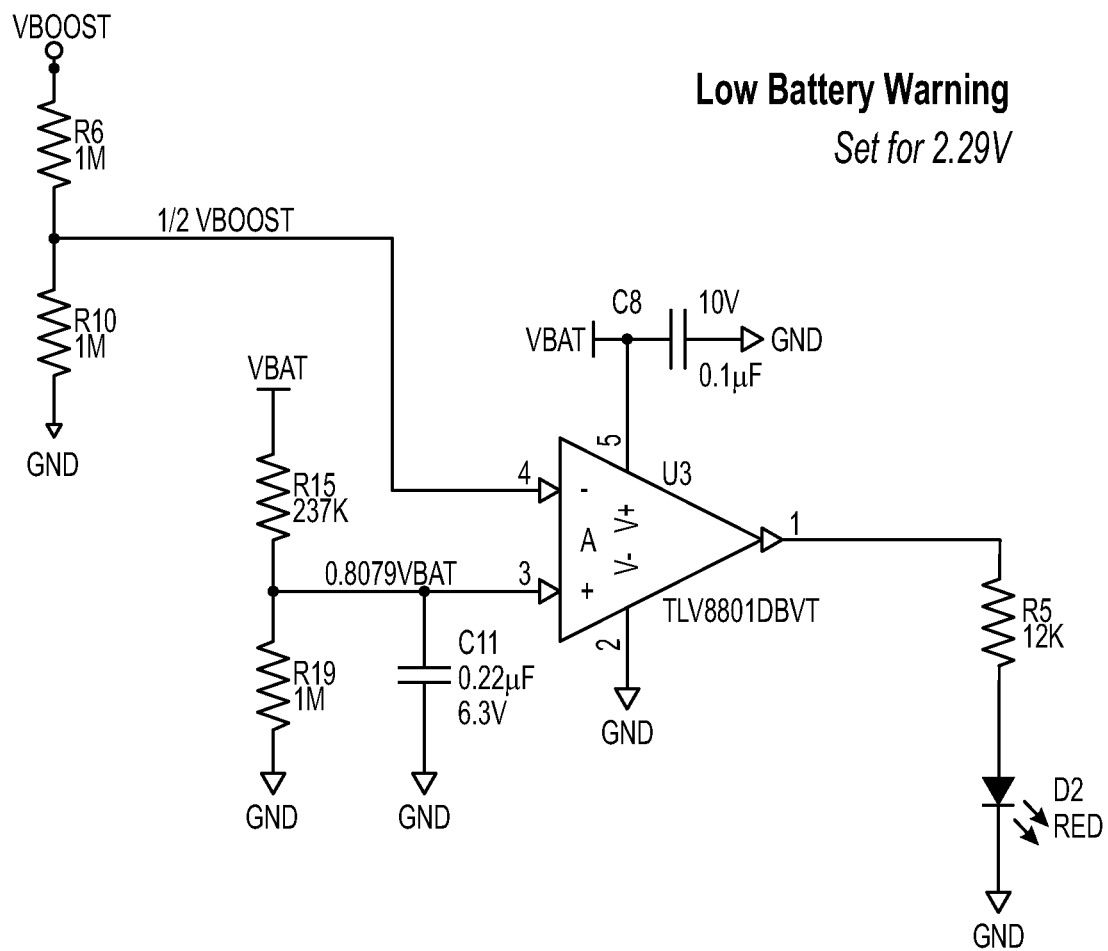
Figure 10:
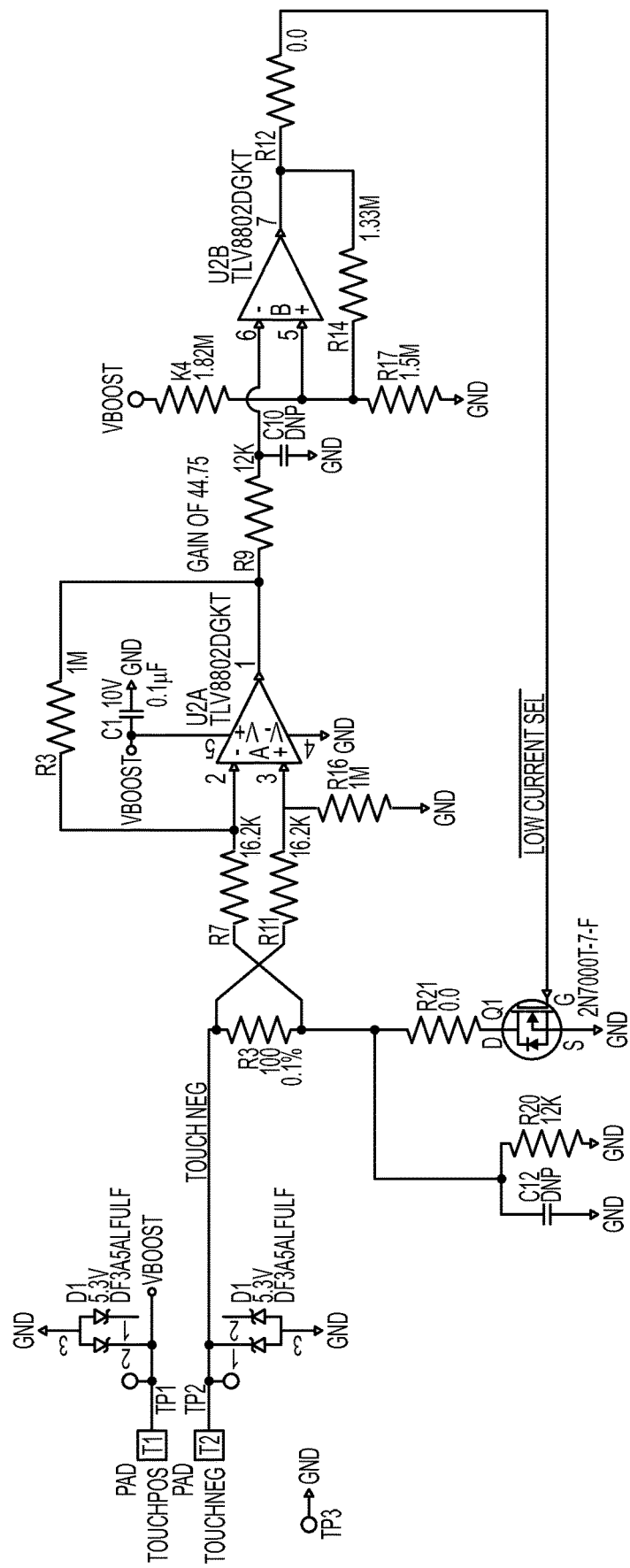
FIG. 10 is an electrical schematic diagram of a current safety switch of the power control circuit in accordance with an embodiment.
Figure 11:
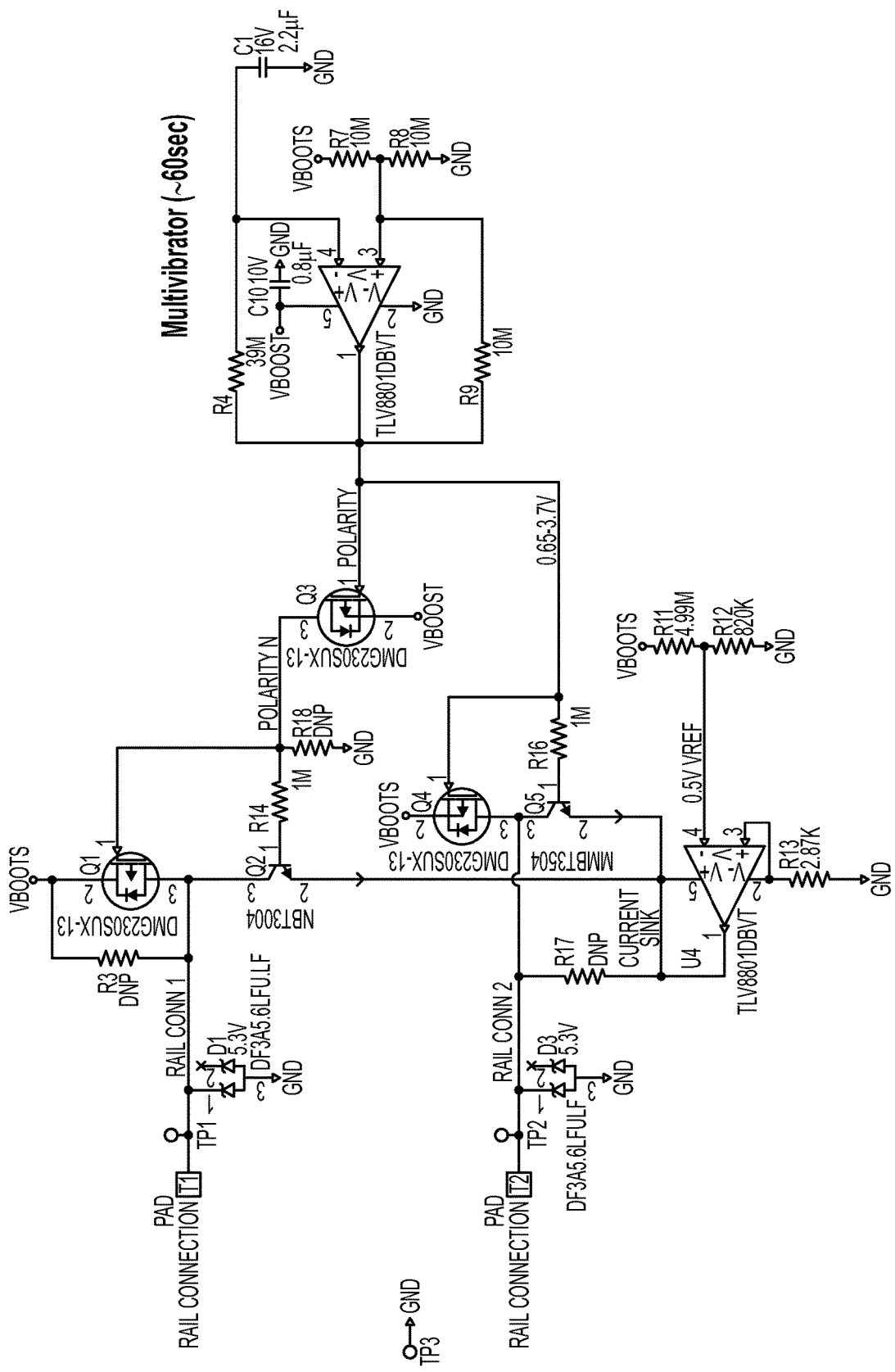
FIG. 11 is an electrical schematic diagram of a multivibrator of the power control circuit in accordance with an embodiment.
Figure 12A:
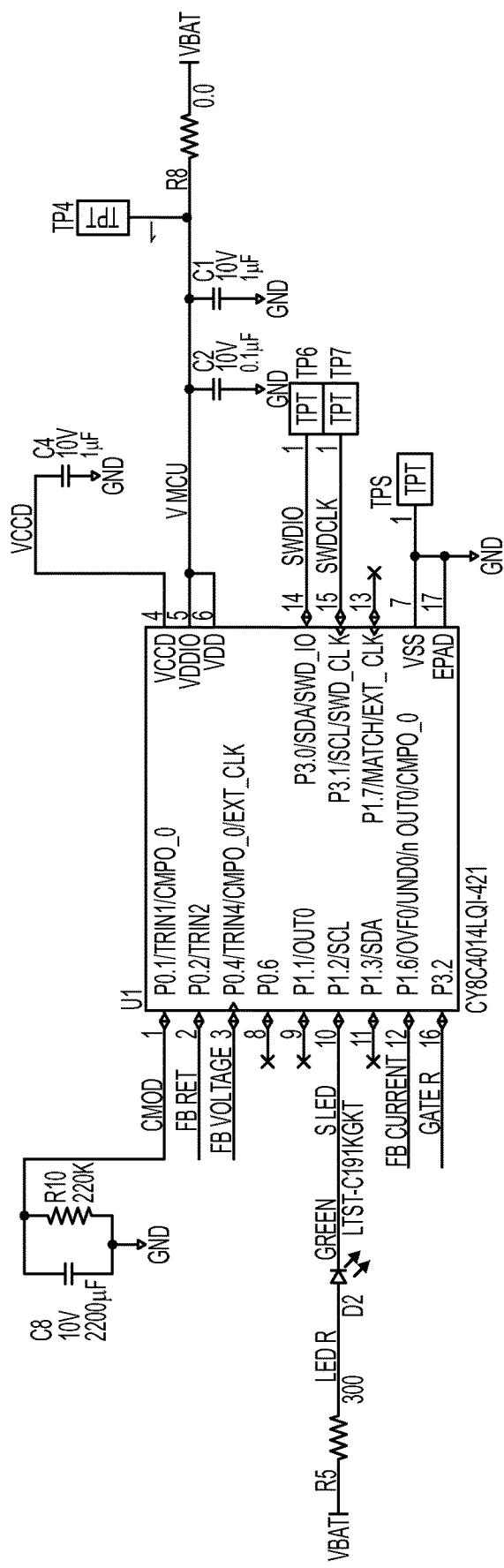
FIG. 12A-12D are electrical schematic diagrams of a microcontroller-based chopper circuit of the power control circuit in accordance with an embodiment.
Figure 12B:
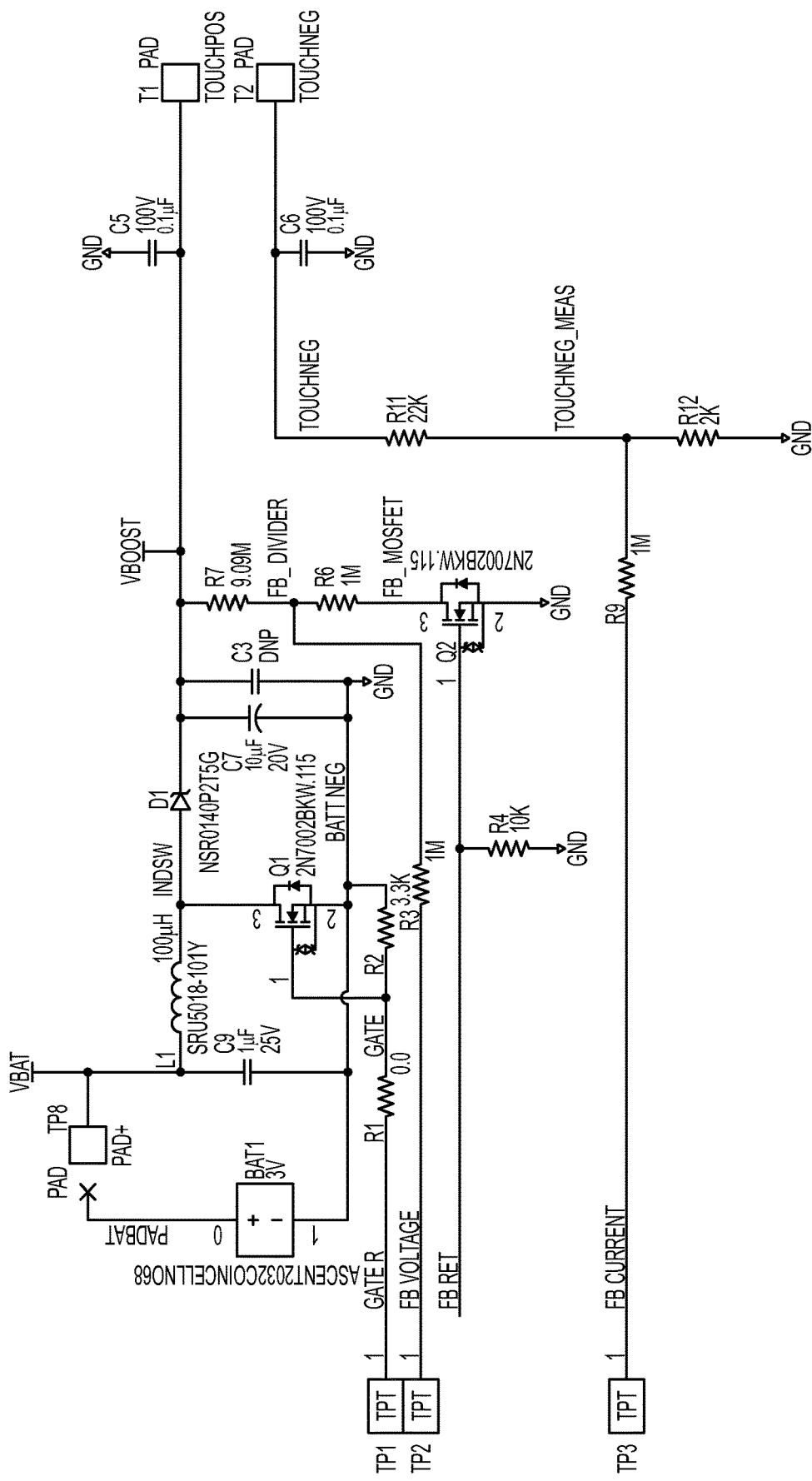
Figure 12C:
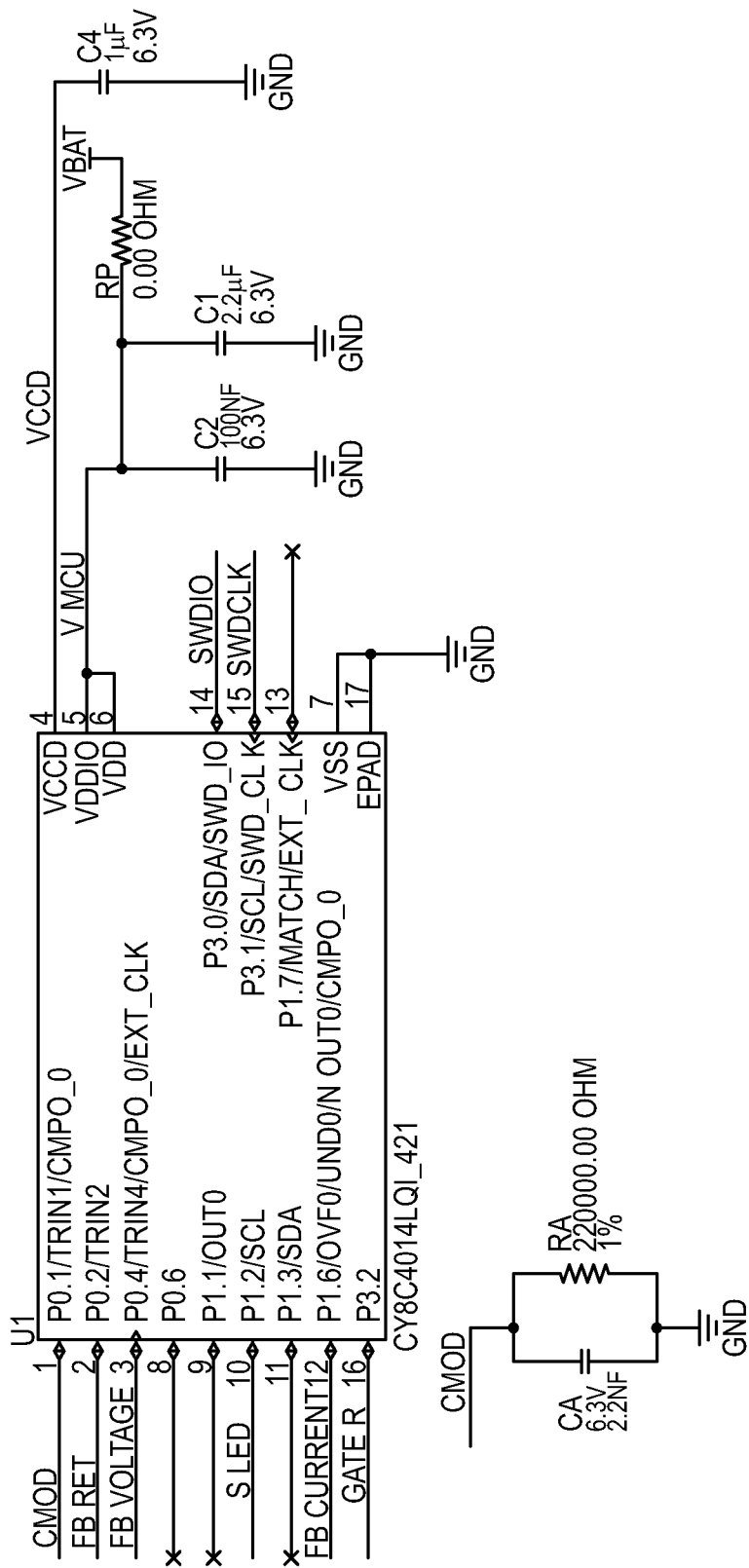
Figure 12D:
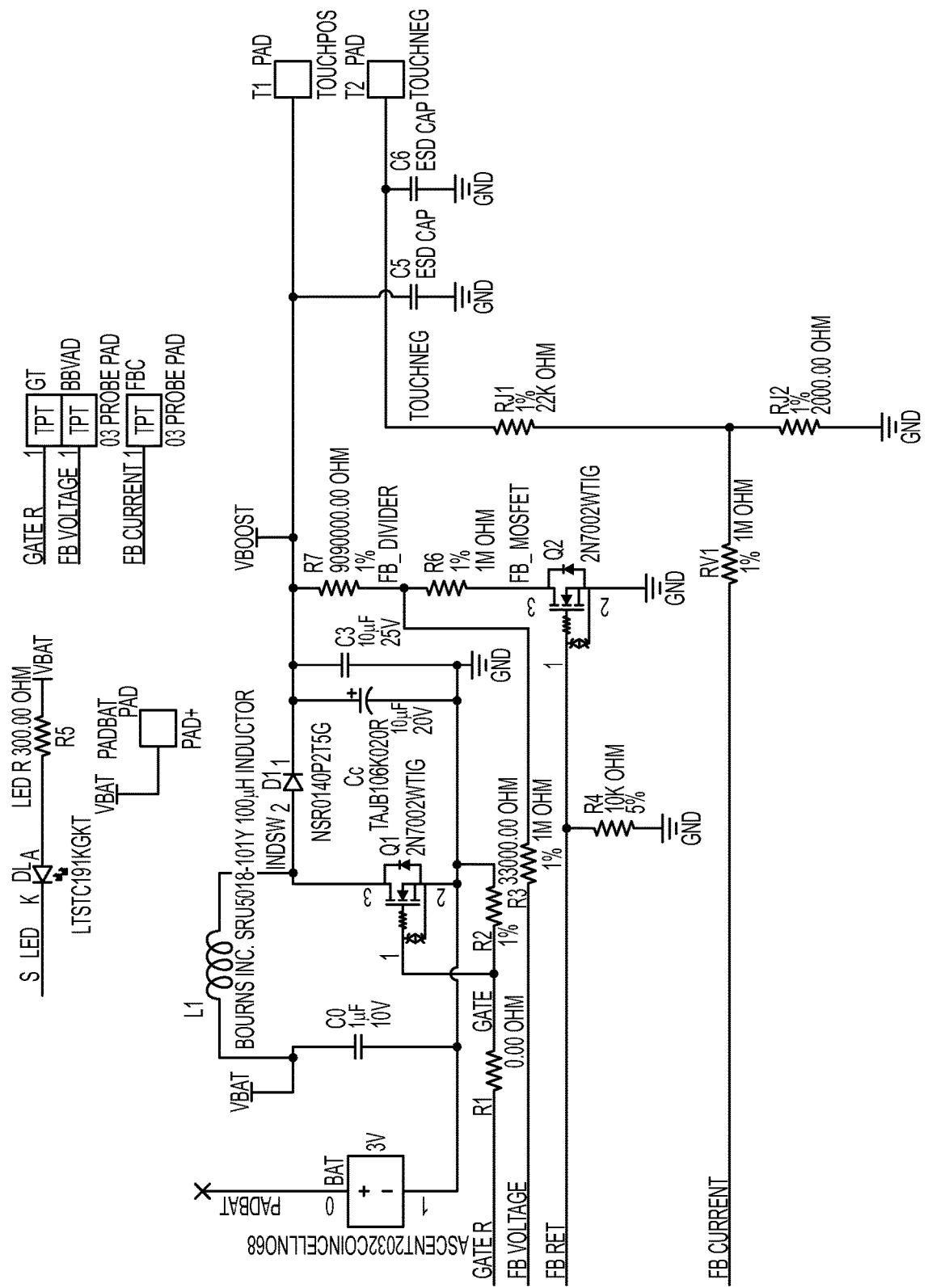

In embodiments, the entire surface device is configured to be periodically replaced and is therefore disposable and/or recyclable. In embodiments, the interior of the power pod structure is not intended to be accessed and the button battery shown in FIG. 7A is not designed to be replaced by a user. Although a user should not be able to access the battery or the electronics that comprise the power control circuit, the power pod may be recycled such that the printed circuit board can be extracted, the battery replaced and the circuit board with the power control circuit and the battery mounted in a new power pod structure to be mated with and secured to the surface device.

In embodiments, a pair of retention posts are configured to secure the circuit board with indicator knockout in the corner of the circuit board configured to be inserted into the interior of the power pod structure with the mating corner structure. In embodiments, the retention posts are generally defined along but on opposite sides of a longitudinal centerline of the power pod structure to provide for more stable, centered and secure retention of both the circuit board within the power pod structure and the power pod structure to the surface structure with a minimum of retention features.

In embodiments, the retention posts have an expandable fixation end that passes through a pair of corresponding contact pads on a lower surface of the circuit board and are used to physically secure the power pod structure to the surface device as shown in FIGS. 5A-5B and 6A-6C. In this embodiment, the surface device may recycled to recover the printed circuit board upon return to a manufacturer or distributor by placing the surface device upside down and cutting the connector bottom of the retention posts from the bottom of the surface device to release the power pod structure from the surface device structure.

In embodiments, an inherent self-registering of the battery case within the battery holder structure pushes battery into the center of the battery holder structure to align and secure the button battery in place using pressure contacts without the need for the battery to be soldered to the printed circuit board.

Referring to the electrical schematics in FIGS. 8A-8B and 9A-9B, electrical schematics show various embodiments of aspects of the power control circuit. Unlike the prior art metal ionic antimicrobial device that relied on a resistor network directly connected to a battery source to provide a selectable output to metal ionic strips forming the antimicrobial surface, in various embodiments a power control circuit is utilizes to manage the battery-powered activation to achieve a more consistent and effective power output that insures a minimum operational duration of at least a month based on operational/run time constraints. The prior art resistor network control of a metal ionic antimicrobial surface would run continuously in response to a microbial contaminant on the surface and would induce variable higher voltages and currents based on the particular requirements of the microbial contaminant. In contrast, in accordance with various embodiments, the power control circuit includes a charge pump that is more efficient and that utilizes a lower sweep current. In some embodiments, the power control circuit is 3.5× more efficient pushing the same amount of current than the prior art device.

In various embodiments, the power control circuit implements a 3.7V-4.2 max voltage for user safety that provides no perceptible shock as demonstrated by various studies. Because the electrical current used in various embodiment is many times less than what is harmful or even perceptible to humans, most user interactions do not perceive the levels of electrical activation that are utilized. It will be understood, however, that individual user perception of electrical activity will vary from person to person, and that for sensitive individual it may vary from an initial perception that may feel like a slight tingling, itching or poking sensation for about half a minute, after which the skin and nervous system will become used to the current and it will be perceived as imperceptible to a user.

In embodiments, the power control circuit includes a current limiting to 450 microamps that causes circuit to limit in response to a dead short of 250 microamps. In various embodiments, the amperage range for the power control circuit ranges from 60 uA to 500 uA. In embodiments depending upon the load of the contaminants on the surface structure, the current drain on the battery may range for 20 uA up to 1.5 mA.

In embodiments, the power control circuit with the voltage booster emulates a constant voltage source within a given voltage tolerance. In embodiments, even though the battery input voltage varies from 1.8V to 3.3V, the VBOOST circuit gives a constant voltage output of 3.7V until the input battery voltage falls below 1.8V.

In embodiments, a Low Battery indicator is implemented to provide a visual indicator of a need to change out the periodically replaceable antimicrobial surface. In some embodiments, the low battery indicator is activated at 10% remaining battery life is target which corresponds to Low Battery Warning at 2.3V that should be about 3 days before a 3V button cell battery input voltage drops below a 2.0V minimum operational threshold.

In embodiments, the power control circuit can be configured to operate in two modes—normal and safety, but there is a period of time where the circuit switches between full and safety mode. Increased current in normal creates oscillation that stems from the droplet nature of the load.

In some embodiments, the power control circuit is configured to operate at 4.3V instead of 3.7, but the power control circuit may be provided with a periodic polarity flip on the leads reverses the ion flow from the silver ions. The periodic polarity flip can also serve as a safety mechanism in addition to, or as an alternative to a safety switch mode. In embodiments, the polarity flip implemented by a multivibrator circuit provides an effective constant current limit of 300 microamps. In embodiments, the polarity inversion may have an inversion cycle every 30-300 seconds. In some embodiments, the inversion cycle is between 40-80 seconds, and more particularly about 60 seconds. In some embodiments, the inversion cycle is between 150-250 seconds, and more particularly between 180-200 seconds. In some embodiments, the polarity inversion has added benefit of providing a visual indication of operational usage of the apparatus. When surface is in active use, the anodic area darkens as silver and copper oxidize when run in one polarity, but not the other. In embodiments, certain of the conductive strips are selectively connected to opposite polarities of the polarity flip to selectively control the darkening of the conductive strips in the pattern to form patterns or even create letters or symbols in the patterns.

It will be understood that the basic underlying technology of the battery-activated metal ionic antimicrobial surfaces developed by the assignee of the present application have been registered for hospital use with the U.S. Environmental Protection Agency as an antimicrobial agent that effectively inhibits the growth of bacteria, fungi, algae, mold, and mildew that can cause unpleasant odors, discoloration, staining, deterioration or corrosion on surfaces to which it is applied, including hospital surfaces (EPA Reg. No. 91681-1). The EPA has not yet reviewed or approved claims that the underlying technology has efficacy against any particular pathogenic microbes. The basic underlying technology has also undergone thorough evaluation, including testing for acute dermal toxicity, oral toxicity, skin irritation, and eye irritation.

Various third-party researchers have conducted a variety of studies and various testing protocols with respect to different aspects and embodiments of the basic underlying technology as reflected in the references set forth below, each of which is incorporated by reference:

1. Disruption of Transmission Network Inhibits Spread of Contamination. "Lamendella study", available from Aionx at "Emanating Efficacy in ICU"
2. Continuous Reduction of Bioburden in ICU. "Esolen—AJIC paper", available from AJIC, article S0196-6553(17)31101-X
3. Bacteria, available from Aionx at "Bacteria lab"
4. Viral
    a. available from Aionx at "AIONX Antimicrobial Technologies Study by Institute for Antiviral Research"
    b. available from Aionx at "REPORT AIONX 2020"
5. C. diff spores. available from Aionx at "C diff lab"
6. Biocompatibility study. available from DTIC at "ADA615774"
7. Reduced Environmental Contamination Correlates with Reduced Infection Rate. available from Tru-D at "BETRD III Rutala 2018"
8. Network Science Used to Inform Infection Prevention Strategies. available from Aionx at "English BMC Infect Dis"
9. Better Environmental Cleaning of High Touch Surfaces Reduces Contamination Throughout Outpatient Facility. available from Aionx at "Reynolds AJIC"

Persons of ordinary skill in the relevant arts will recognize that embodiments may comprise fewer features than illustrated in any individual embodiment described above. The embodiments described herein are not meant to be an exhaustive presentation of the ways in which the various features of the embodiments may be combined. Accordingly, the embodiments are not mutually exclusive combinations of features; rather, embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted. Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended. Furthermore, it is intended also to include features of a claim in any other independent claim even if this claim is not directly made dependent to the independent claim.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of Section 112, sixth paragraph of 35 U.S.C. are not to be invoked unless the specific terms "means for" or "step for" are recited in a claim.

The invention claimed is:

1. An apparatus that provides a metal ionic antimicrobial surface configured for external use on a surface location in an indoor environment, the apparatus comprising:
   a surface structure defining a pair of opposed surfaces separated by a thickness, the surface structure having:
      a first of the pair of opposed surfaces that forms a base material layer configured to be positioned on at least a portion of the surface location;
      a second of the pair of opposed surfaces that forms an exposed layer having a pattern of conductive strips separated by corresponding insulative spacings between adjacent conductive strips wherein an average width of each conductive strip and each insulative spacing is between 0.1 to 0.5 millimeters; and
      an insulating layer disposed between the base material layer and the exposed layer; and
   a power pod structure physically secured to the surface structure on a portion of the exposed layer, the power pod structure housing:
   a battery having an amp-hour electrical storage capacity of between 150 to 1500 mAh; and
   a power control circuit that is electrically connected to the battery and to the conductive strips on the exposed layer, the power control circuit including a voltage booster circuit configured to provide a constant low direct-current voltage of between about 2.5V to 4.5V to achieve a replaceable period of at least a month,
   such that electrical activation of the conductive strips generates an active oligodynamic effect on the surface structure that produces a reduction in microbial contaminants over the replaceable period when the metal ionic antimicrobial surface is positioned on the surface location in a zone that correlates to high impact regions for transmission pathways of microbial contaminants in the indoor environment.

2. The apparatus of claim 1, wherein the environment is in a health-related indoor environment and the reduction in microbial contaminants is a generally continuous and consistent reduction over the replaceable period.

3. The apparatus of claim 2, wherein the generally continuous and consistent reduction is a reduction of at least 99% in microbial contaminants on the metal ionic antimicrobial surface following a predetermined period after exposure to such microbial contaminants.

4. The apparatus of claim 2, wherein the generally continuous and consistent reduction is a reduction of at least a 2× reduction in a number of other contaminated surfaces within the zone.

5. The apparatus of claim 4, wherein the zone is defined by a radius of up to 5 m from the metal ionic antimicrobial surface.

6. The apparatus of claim 1, wherein the power pod structure is self-contained and the battery is not configured for replacement by a user.

7. The apparatus of claim 1, wherein the battery is a coin-type battery having an amp-hour electrical storage capacity between 500-750 mAH.

8. The apparatus of claim 1, wherein the power control circuit further comprises a current limiting circuit to limit a current to conductive strips of to less than 430 microamps.

9. The apparatus of claim 1, wherein the power control circuit further comprises a polarity inversion circuit that inverts a polarity of a current to the conductive strips during an inversion cycle of every 30-300 seconds.

10. The apparatus of claim 1, wherein the inversion cycle is between 180-200 seconds.

11. The apparatus of claim 1, wherein the conductive strips are formed of a polymer material doped with metallic elements consisting of particles or flakes.

12. The apparatus of claim 11, wherein the metallic elements are screen printed on the exposed layer of the surface structure.

13. The apparatus of claim 11, wherein the metallic elements are comprised of a mixture of silver and copper.

14. The apparatus of claim 11, wherein the polymer material is a metallic doped polymer.

15. The apparatus of claim 14, wherein the metallic doped polymer comprises silver in a range of about 20-30% and copper in a range of about 65%-75% of a 90-95% cured metallic polymer.

16. The apparatus of claim 1, wherein the power pod structure has a volume that ranges from 100-250 cubic centimeters.

17. The apparatus of claim 1, wherein the power pod structure includes a mating structure that is sufficiently flexible to be pressure mounted to the surface structure.

18. An apparatus that provides a metal ionic antimicrobial surface configured for external use on a surface location in an indoor environment, the apparatus comprising:
   a surface structure defining a pair of opposed surfaces separated by a thickness, the surface structure having:
      a first of the pair of opposed surfaces that forms a base material layer configured to be positioned on at least a portion of the surface location;
      a second of the pair of opposed surfaces that forms an exposed layer having a pattern of conductive strips formed of a polymer material doped with metallic elements consisting of particles or flakes of a mixture of silver and copper in a metallic doped polymer, the conductive strips being separated by corresponding insulative spacings between adjacent conductive strips; and
      an insulating layer disposed between the base material layer and the exposed layer; and
   a power pod structure that is self-contained with a volume of less than 250 cubic centimeters, the power pod structure housing:
      a battery having an amp-hour electrical storage capacity of less than 750 mAh; and
      a power control circuit that is electrically connected to the battery to provide a low voltage direct current output to the conductive strips on the exposed layer, the power control circuit including a polarity inversion circuit that inverts a polarity of a current to the conductive strips during an inversion cycle of every 30-300 seconds to achieve a replaceable period of at least a month, such that electrical activation of the conductive strips generates an active oligodynamic effect on the surface structure that produces a reduction in microbial contaminants over the replaceable period.

19. The apparatus of claim 18, wherein the power pod structure is physically secured to the surface structure on a portion of the exposed layer.

\* \* \* \* \*